United States Patent
O Ruanaidh

(10) Patent No.: US 9,275,465 B2
(45) Date of Patent: Mar. 1, 2016

(54) SYSTEM FOR PREPARING AN IMAGE FOR SEGMENTATION

(75) Inventor: Joseph J. O Ruanaidh, Hamilton, NJ (US)

(73) Assignee: GE Healthcare Bio-Sciences Corp., Malborough, MA (US)

(*) Notice: Subject to any disclaimer, the term of this patent is extended or adjusted under 35 U.S.C. 154(b) by 1129 days.

(21) Appl. No.: 12/296,319

(22) PCT Filed: Apr. 18, 2007

(86) PCT No.: PCT/US2007/066829
§ 371 (c)(1),
(2), (4) Date: Oct. 7, 2008

(87) PCT Pub. No.: WO2007/121454
PCT Pub. Date: Oct. 25, 2007

(65) Prior Publication Data
US 2009/0074275 A1 Mar. 19, 2009

Related U.S. Application Data

(60) Provisional application No. 60/745,022, filed on Apr. 18, 2006.

(51) Int. Cl.
*A61B 5/00* (2006.01)
*G06T 7/00* (2006.01)
*G06T 7/40* (2006.01)

(52) U.S. Cl.
CPC .............. *G06T 7/0081* (2013.01); *A61B 5/726* (2013.01); *G06T 7/0087* (2013.01); *G06T 7/402* (2013.01); *G06T 2207/10056* (2013.01); *G06T 2207/20064* (2013.01); *G06T 2207/30024* (2013.01)

(58) Field of Classification Search
CPC ................... G06T 2207/20064; G06T 5/002; A61B 5/726
USPC .................................. 382/133, 128, 240, 124
See application file for complete search history.

(56) References Cited

U.S. PATENT DOCUMENTS 5,186,173 A * 2/1993 Zuckerman .................... 600/329
5,507,287 A * 4/1996 Palcic et al. .................... 600/317
(Continued)

FOREIGN PATENT DOCUMENTS

EP         1 355 271          12/2005
WO    WO 03095986 A1 *  11/2003

OTHER PUBLICATIONS

Selesnick et al., The Dual-Tree Complex Wavelet Transform, Nov. 2005, IEEE Signal Processing Magazine, vol. 22 Issue:6, pp. 123-151.*

(Continued)

*Primary Examiner* — Matthew Bella
*Assistant Examiner* — Dennis Rosario

(57) ABSTRACT

A system for cleaning up and preparing an image for segmentation is disclosed. An image transmitting device is configured to transmit a first image to an image receiving device. The image receiving device is configured to: receive the first image; apply a Dual Tree Complex Wavelet transform to the first image to form a plurality of sub-images; generate a high pass image based on the plurality of sub-images; generate a rotational invariant resultant image based on the high pass image; generate a low pass image based on the plurality of sub-images; and combine the rotational invariant resultant image and the low pass image to form a pseudo-fluorescent image.

23 Claims, 12 Drawing Sheets

(56) References Cited

U.S. PATENT DOCUMENTS

| | | | |
|---|---|---|---|
| 5,687,716 A * | 11/1997 | Kaufmann et al. | 600/300 |
| 6,054,711 A * | 4/2000 | Bruening et al. | 250/339.08 |
| 6,136,540 A * | 10/2000 | Tsipouras et al. | 435/6.16 |
| 6,243,492 B1 * | 6/2001 | Kamei | 382/181 |
| 6,292,575 B1 | 9/2001 | Bortolussi et al. | |
| 6,539,115 B2 * | 3/2003 | Fujimoto et al. | 382/225 |
| 7,079,686 B2 * | 7/2006 | Ahmed et al. | 382/176 |
| 2004/0114800 A1 * | 6/2004 | Ponomarev et al. | 382/173 |
| 2005/0259889 A1 | 11/2005 | Ferrari et al. | |
| 2006/0217594 A1 * | 9/2006 | Ferguson | 600/175 |

OTHER PUBLICATIONS

Sendur et al., Multiple Hypothesis Mapping of Functional MRI Data in Orthogonal and Complex Wavelet Domains, Sep. 2005, IEEE Transactions on Signal Processing, vol. 53 Issue: 9, pp. 3413-3426.*

Hatipoglu et al., Texture Classification using Dual-Tree Complex Wavelet Transform, Seventh International Conference on (Conf. Publ. No. 465) Image Processing and Its Applications [on-line], Jul. 1999, vol. 1, pp. 344-347. Retrieved from http://ieeexplore.ieee.org/xpls/abs_all.jsp?arnumber=791409&tag=1.*

O'Callaghan et al., Combined Morphological-Spectrum Unsupervised Image Segmentation [on-line], Jan. 2005 [retrieved Jun. 8, 2015], IEEE Transactions on Image Processing, vol. 14, No. 1, pp. 49-62. Retrieved from the Internet: http://ieeexplore.ieee.org/xpls/abs_all.jsp?arnumber=1369329.*

Hill, P., et al., "Rotationally invariant texture features using the dual-tree complex wavelet transform" Image Processing, 2000, Proceedings. 2000 International Conference on Sep. 10-13, 2000, Piscataway, NJ, USA, IEEE, vol. 3, Sep. 10, 2000, pp. 901-904.

Lu, J., et al., "Contrast Enhancement of Medical Images Using Multiscale Edge Representation" Optical Engineering, Soc. of Photo-Optical Instrumentation Engineers. Bellingham, US, vol. 33, No. 7, Jul. 1, 1994, pp. 2151-2161.

Vuylsteke, P., et al., "Multiscale Image Contrast Amplification (MUSICA)" Proc. SPIE, Medical Imaging 1994: Image Processing, vol. 2167, May 1994, pp. 551-560.

Burgiss, S., et al., Digital Signal Processing, vol. 8, No. 4, (1998) 267-276.

Cho, D., et al., Signal Processing: Imagine Communication, vol. 20, No. 1, (2005) 77-89.

Hill, P., et al., Image Processing, vol. 3, (2000) 901-904.

Hill, P., "Wavelet Based Texture Analysis and Segmentation for Image Retrieval and Fusion", Feb. 2002, retrieved from the internet: URL:http://www.tallypaul.pwp.blueyonder.co.uk/papers/thesis.pdf [retrieved on Feb. 9, 2012].

Kato, Z., et al., Computer Analysis of Images and Patterns, 9th International Conference, CAIP 2001. Proceedings (Lecture Notes in Computer Science vol. 2124), 2001, pp. 547-554.

Kokare, M., et al., International Conference on Image Processing, 2004, vol. 1, pp. 393-396.

Lu, J., et al., Optical Engineering, vol. 33, No. 7 (1994) 2151-2161.

Okazaki, H., et al., Electronics and Communications in Japan, Part 3, vol. 87, No. 4, part 3 (2004) 40-54.

Porter, R., et al., IEEE Transactions on Image Processing, vol. 5, No. 4 (1996) 662-665.

Rangarajan, R., et al., "Image Denoising Using Wavelets—Wavelets and Time Frequency", Dec. 16, 2002, Retrieved from the internet URL:http://citeseerx.ist.psu.edu/viewdoc/download?doi=10.1.1.152.5399&rep=rep1&type=pdf [retrieved on Jul. 3, 2012].

Selesnick, I., International Conference on Image Processing (ICIP), vol. 3 (2002) 573-576.

Sendur, L., et al., IEEE Transactions on Signal Processing, vol. 50, No. 11 (2002) 2744-2756.

Vuylsteke, P., et al. Proceedings of SPIE, vol. 2167 (1994) 551-560.

Extended EP Search Report issued on co-pending EP application No. 11150001.3 dated Sep. 4, 2012.

* cited by examiner

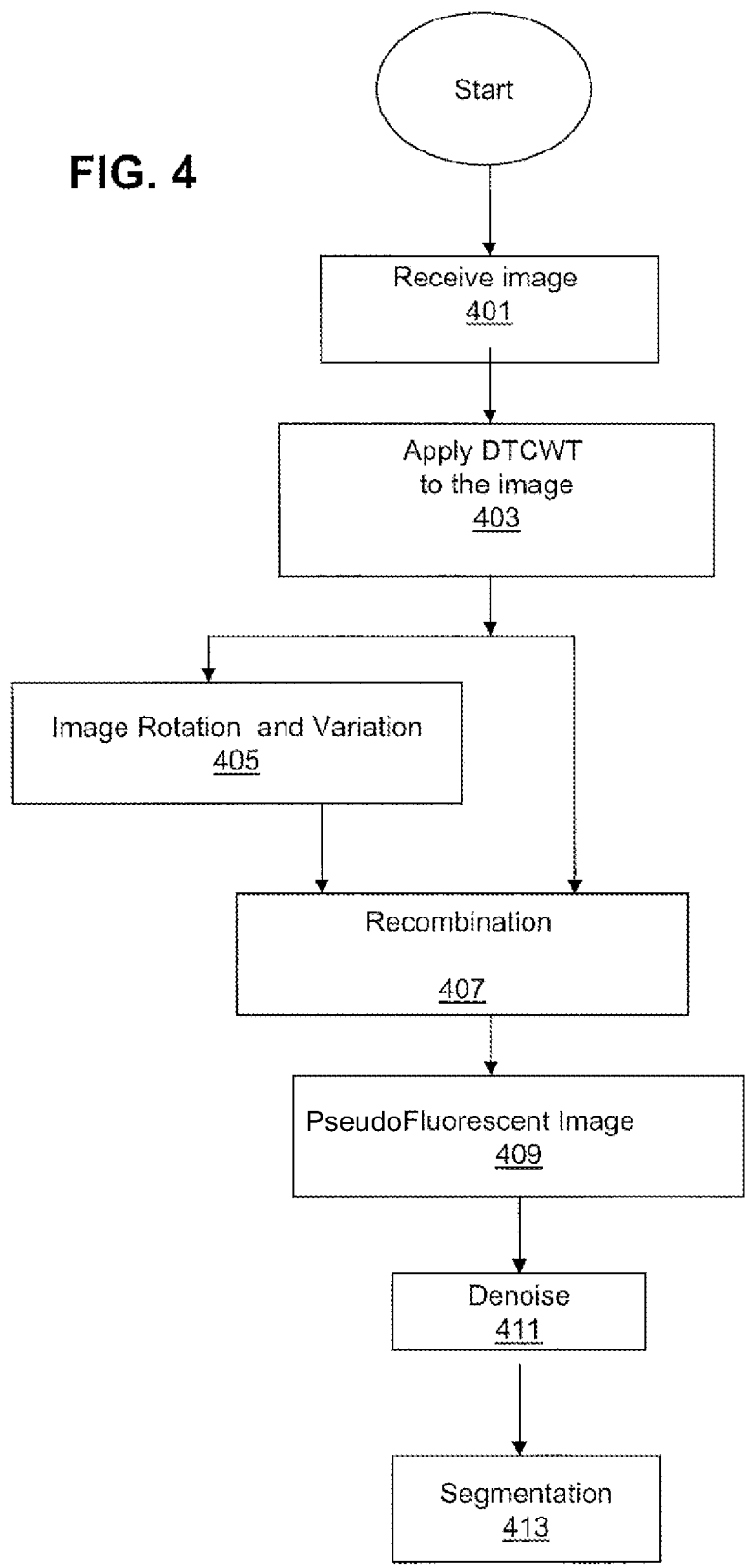

FIG. 5A
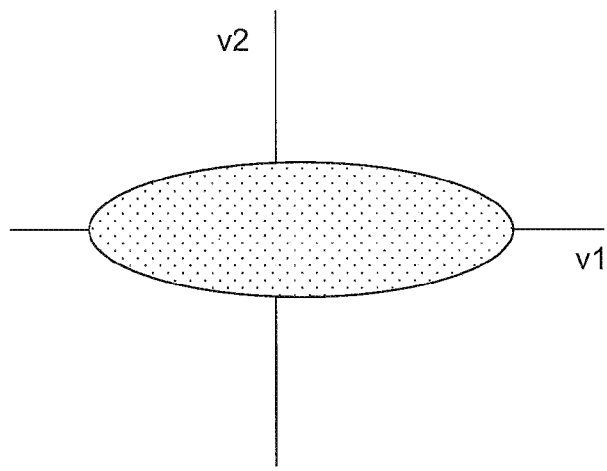
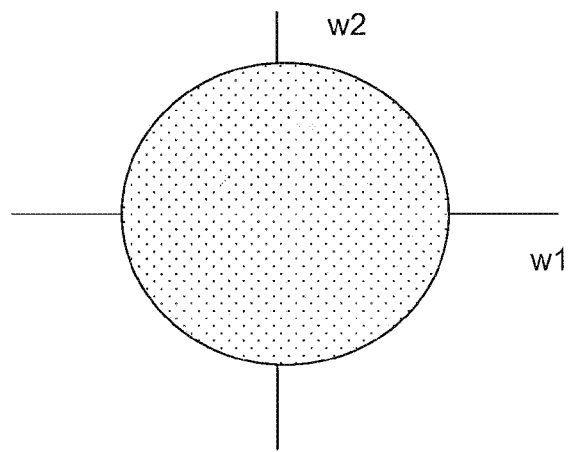
FIG. 5B

FIG. 7
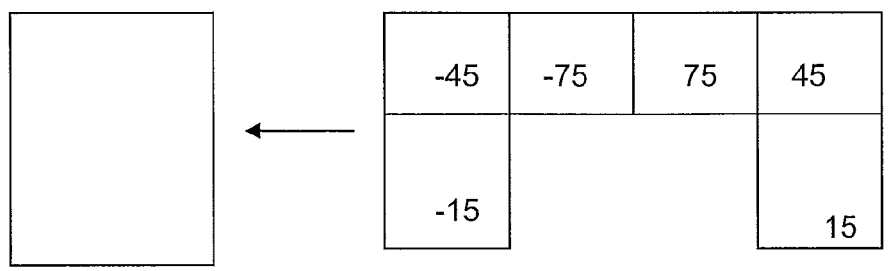
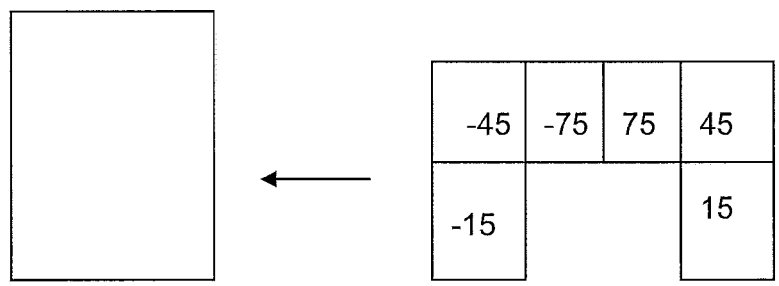
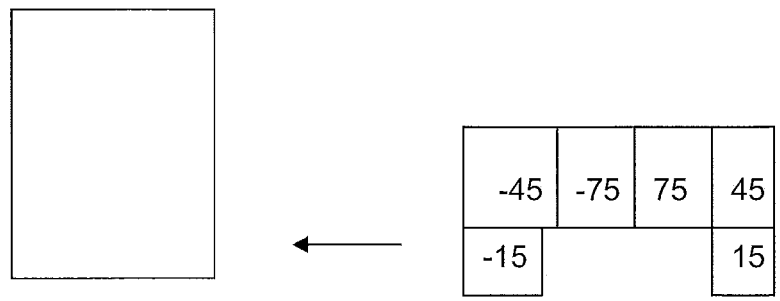

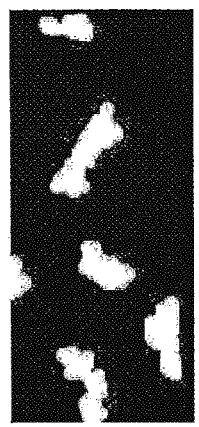
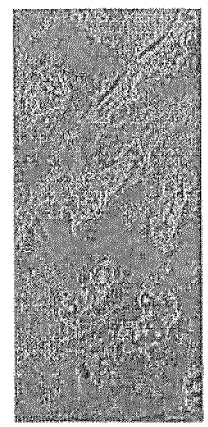
Figure 10a
Figure 10b

SYSTEM FOR PREPARING AN IMAGE FOR SEGMENTATION

CROSS-REFERENCE TO RELATED APPLICATIONS

This application is a filing under 35 U.S.C. §371 and claims priority to international patent application number PCT/US2007/066829 filed Apr. 18, 2007, published on Oct. 25, 2007, as WO 2007/121454, which application claims priority to U.S. provisional patent application No. 60/745,022 filed Apr. 18, 2006; the entire disclosure of which is incorporated herein by reference in its entirety.

FIELD OF THE INVENTION

This invention relates to a system for preparing an image for segmentation.

BACKGROUND OF THE INVENTION

Generally, when live cells or microorganisms are examined to determine their characteristics they are placed under a microscope for analysis. Live cells are analyzed to find cures for many illnesses or diseases that exist today, such as cancer. For example, a person or scientist may put a breast lymph node cell on a specimen plate under a microscope to determine how the lymph node cell functions under various conditions in order to discover a method for treating the lymph node cell so it will not be cancerous.

A microscope that may be utilized to view cell function is a fluorescent microscope and the like. The typical fluorescent microscope utilizes a light source to transmit light through a dichroic mirror to excite fluorescent dyes in stained living cells or a sample specimen that absorbs radiation from the light and emits radiation at a lower frequency, whereby this emitted light will be reflected back through the dichroic mirror to an optical detector. The optical detector will then receive an image of the living cells. Normally, the optical detector will send the image to a computer that would reconstruct the image of the living cells based on an algorithm or equation.

Alternatively, one can use microscopy techniques other than fluorescence to view the cells, such as phase contrast microscopy, differential interference (DIC) microscopy, brightfield transmitted light microscopy and the like. Phase contrast microscopy is a contrast enhancing optical technique that can be utilized for generating high-contrast images of transparent specimens such as living cells, microorganisms and sub-cellular particles. This phase contrast technique employs an optical mechanism to translate minute variations in phase into corresponding changes in amplitude, which can be visualized as differences in image contrast. This type of microscopy enables one to observe low-contrast specimens that are either transparent or semi-transparent, which is often difficult, especially without proper illumination. The application of suitable contrast enhancement provides a substantial increase in contrast of barely visible low-contrast specimens in positive or negative relief. The illumination utilized by the phase contrast microscopy is standard brightfield transmitted light, oblique brightfield transmitted light and single-sided darkfield illumination. When a person utilizes standard brightfield transmitted light for illumination he avoids harmful exposure of the specimens to toxic dyes associated with staining living cells so the specimens will not die. However, the problem with utilizing this type of illumination is that brightfield images of the specimens look colorless and washed out. Moreover, in order to ensure that the specimen does not die it is necessary to keep the level of exposure the specimen receives from harmful light and bleaching to a minimum. Moreover, low intensity inevitably leads to noise being a severe problem.

Differential Interference Contrast (DIC) microscopy is a mechanism for increasing contrast in transparent specimens. DIC microscopy is a beam-shearing interference system in which the reference beam is sheared by a miniscule amount. This technique produces a monochromatic shadow-cast image that effectively displays the gradient of optical paths for both high and low spatial frequencies present in the specimen. The regions of the specimen where the optical paths increase along a reference direction appear brighter (or darker), while regions where the path differences decrease appear in reverse contrast. As the gradient of optical path difference grows steeper, image contrast is dramatically increased. Also, this type of microscopy enables one to observe low-contrast specimens that are either transparent or semi-transparent, which is often difficult especially without proper illumination. This DIC microscopy also utilizes standard brightfield transmitted light that causes the same problems discussed above for the phase contrast microscopy.

For brightfield transmitted light microscopes, light is aimed toward a lens beneath a stage called the condenser, through the sample specimen, through an objective lens, and to the eye through a second magnifying lens, the ocular or eyepiece. The object to be inspected is normally placed on a clear glass slide and light is transmitted through the object, which makes the object appear against a bright background hence the term "brightfield." The objects in the light path are seen because natural pigmentation or stains absorb light differentially, or because they are thick enough to absorb a significant amount of light despite being colorless. The interior of the cells in the brightfield image is barely discernible so one can not tell the difference between the cells and the background. Also, the noise is a severe problem which inhibits segmentation of the cell. If one could segment cells in such brightfield images this would provide a wealth of information about cells that can be used as a diagnostic tool. For example, the utilization of the brightfield imaging technique is very useful in cancer research because this technique allows cancer cells to be kept alive, which is necessary in order to perform cancer research. On the other hand, when other imaging techniques are utilized living cells are killed when they are stained, which prohibits scanning of cells for cancer research.

In order to detect, diagnose and treat living cells in brightfield images these cells, such as cancer cells must be analyzed by segmenting and reconstructing the image of living cells. Therefore, there is a need for a system that is able to analyze living cells in brightfield images where the living cells can be discerned from the background of the sample specimen.

BRIEF SUMMARY OF THE INVENTION

The present invention has been accomplished in view of the above-mentioned technical background, and it is an object of the present invention to provide a simple method for preparing an image for segmentation.

In a preferred embodiment of the invention, a system for preparing an image for segmentation is disclosed. An image transmitting device is configured to transmit a first image to an image receiving device. The image receiving device is configured to: receive the first image; apply a Dual Tree Complex Wavelet transform to the first image to form a plurality of sub-images; generate a high pass image based on the plurality of sub-images; generate a rotational invariant resultant image based on the high pass image; generate a low pass image based on the plurality of sub-images; and combine the rotational invariant resultant image and the low pass image to form a pseudo-fluorescent image.

In another preferred embodiment of the invention, an apparatus for preparing an image for segmentation is disclosed. A connection interface is configured to receive a first image; the connection interface is coupled to a mass storage, wherein the mass storage is configured to: receive the first image; apply a Dual Tree Complex Wavelet transform to the first image to form a plurality of sub-images; generate a high pass image based on the plurality of sub-images; generate a rotational invariant resultant image based on the plurality of sub-images; generate a low pass image based on the plurality of sub-images; and combine the rotational invariant resultant image and the low pass image to form a pseudo-fluorescent image.

In another preferred embodiment of the invention, a method for preparing an image for segmentation is disclosed. A first image is received. A Dual Tree Complex Wavelet Transform is applied to the first image to form a plurality of sub-images. A high pass image is generated based on the plurality of sub-images. A rotational invariant resultant image is generated based on the high pass image A low pass image is generated based on the plurality of sub-images. The rotational invariant resultant image and the low pass image are combined to form a pseudo-fluorescent image.

In yet another preferred embodiment of the invention, a computer-readable medium that is configured to prepare an image for segmentation is disclosed. A first image is received. A Dual Tree Complex Wavelet Transform is applied to the first image to form a plurality of sub-images. A high pass image is generated based on the plurality of sub-images. A rotational invariant resultant image is generated based on the high pass image. A low pass image is generated based on the plurality of sub-images. The rotational invariant resultant image and the low pass image are combined to form a pseudo-fluorescent image.

BRIEF DESCRIPTION OF THE DRAWINGS

These and other advantages of the present invention will become more apparent as the following description is read in conjunction with the accompanying drawings.

FIG. 4 depicts a flow chart of how an image is prepared for segmentation in accordance with the invention.

FIG. 5A depicts feature vectors of the image of FIG. 3 in accordance with the invention.

FIG. 5B depicts whitened feature vectors of the image of FIG. 3 in accordance with the invention.

FIG. 7 illustrates decompositions of sub-images and resealing of the image of FIG. 6 in accordance with the invention.

FIG. 10A is an example of the brightfield image of FIG. 3 that is transformed into a pseudo-fluorescent image in accordance with the invention.

FIG. 10B is another example of a brightfield image where the image has been transformed into a pseudo-fluorescent image.

DETAILED DESCRIPTION OF THE INVENTION

The presently preferred embodiments of the invention are described with reference to the drawings, where like components are identified with the same numerals. The descriptions of the preferred embodiments are exemplary and are not intended to limit the scope of the invention.

Figure 1:
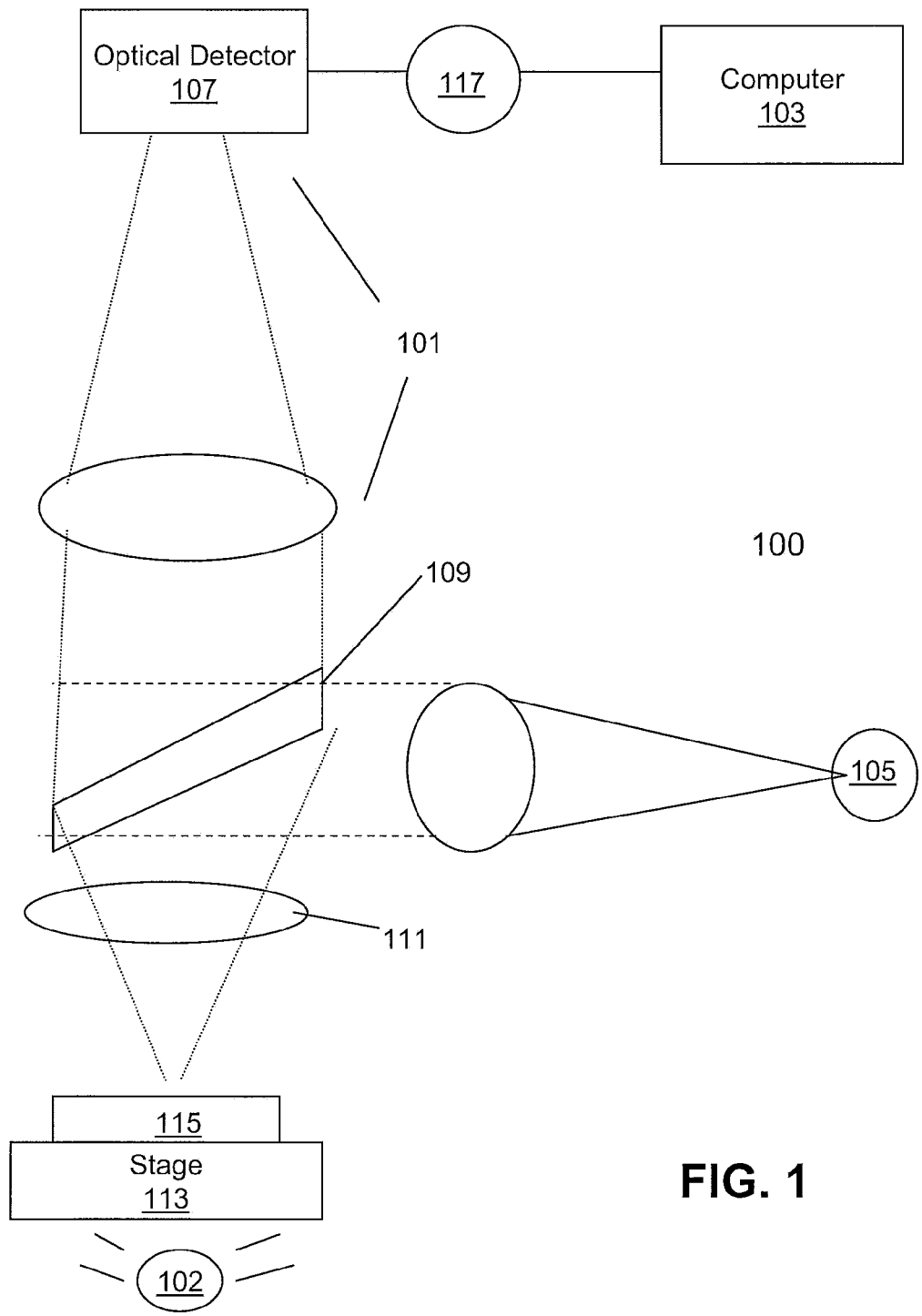
FIG. 1 illustrates a block diagram of a segmentation system in accordance with an embodiment of the invention.

FIG. 1 illustrates a block diagram of a segmentation system of the invention. This segmentation system 100 includes a conventional fluorescent microscope system 101 electrically or wirelessly connected by a communication link 117 to a conventional computer 103. The communication link 117 may be a local access network (LAN), a wireless local network, a wide area network (WAN), a metropolitan area network, a virtual area network, a universal service bus (USB), an Ethernet link, a satellite link, cable, cellular, twisted-pair, fiber-optic or any network that is able to facilitate the transfer of data between the fluorescent microscope system 101 and the computer 103. Fluorescent microscope system 101 includes a light source 105, an optical detector 107, a scanning mirror 109, an objective lens 111, an object stage 113 and a sample specimen 115. Fluorescent microscope system 100 may be referred to as an image transmitting device that is capable of capturing an image, by utilizing the optical detector 107, of the sample specimen 115 or any type of object that is placed on the object stage 113. The sample specimen 115 may be live biological organisms, biological cells, bacteria, De-Ribo Nucleic Acid, nucleic acid or the like. The fluorescent microscope system 101 may be a typical fluorescent microscope, phase contrast microscope, differential interference contrast microscope, or a microscope known to those of ordinary skill in the art. In another embodiment, the fluorescent microscope system 101 may be a typical high throughput assay that is able to rapidly detect, analyze and provide images of biological organisms or the like.

The light source 105 may be a laser, a plurality of lasers or any type of lighting device known to those of ordinary skill that provides excitation light to force the fluorescent dyes in the sample specimen 115 to emit light from the stained portions of the sample specimen 115. Typically, before the sample specimen 115 is placed on the object stage 113 fluorescent dye molecules are inserted into the sample specimen 115 or the sample specimen is stained, whereby when the excitation light of the light source 105 contacts the sample specimen 115 then the fluorescent dyes in the sample specimen 115 absorb the light or radiation of the frequency of the light and emit an illumination light or radiation at a lower fixed frequency. In another embodiment, this microscope is a brightfield microscope, where light 102 is aimed toward a lens beneath the object stage 113 called the condenser (not shown), through the sample specimen 105, through the objective lens 111, and to the eye through a second magnifying lens, the ocular or key piece as described previously. Scanning mirror 109 is located above the sample 115, this scanning mirror 109 operates as a typical scanning mirror that is able to receive the light or excitation light from the light source 105, then transfer the light through the objective lens to cause the fluorescent dye in the sample specimen 115 to emit fluorescent light or illumination light that is transmitted back through the objective lens 111 and the scanning mirror 109 to the optical detector 107. For the fluorescent microscope, the scanning mirror 109 may also be referred to as a dichroic mirror 109, which reflects light shorter than a certain wavelength and passes light longer than that wavelength. The optical detector 107 that receives the illumination light may be a photomultiplier tube, a charged coupled device (CCD), a complementary metal-oxide semiconductor (CMOS) image detector or any optical detector utilized by those of ordinary skill in the art. Optical detector 107, as stated above, is electrically or wirelessly connected by the communication link 117 to the computer 103.

The computer 103 may be referred to as an image receiving device 103, image detection device 103 or a high throughput screening device. In another embodiment of the invention, image receiving device 103 may be located inside of the image transmitting device 101. The image receiving device 103 acts as a typical computer, which is capable of receiving an image of the sample specimen 115 from the optical detector 107, then the image receiving device 103 is able to build up or reconstruct the image by utilizing a standard image processing software program, algorithm or equation usually one pixel at a time. Also, the computer 103 may be a personal digital assistant (PDA), laptop computer, notebook computer, mobile telephone, hard-drive based device or any device that can receive, send and store information through the communication link 117. Although, one computer is utilized in this invention a plurality of computers may be utilized in place of computer 103.

Figure 2:
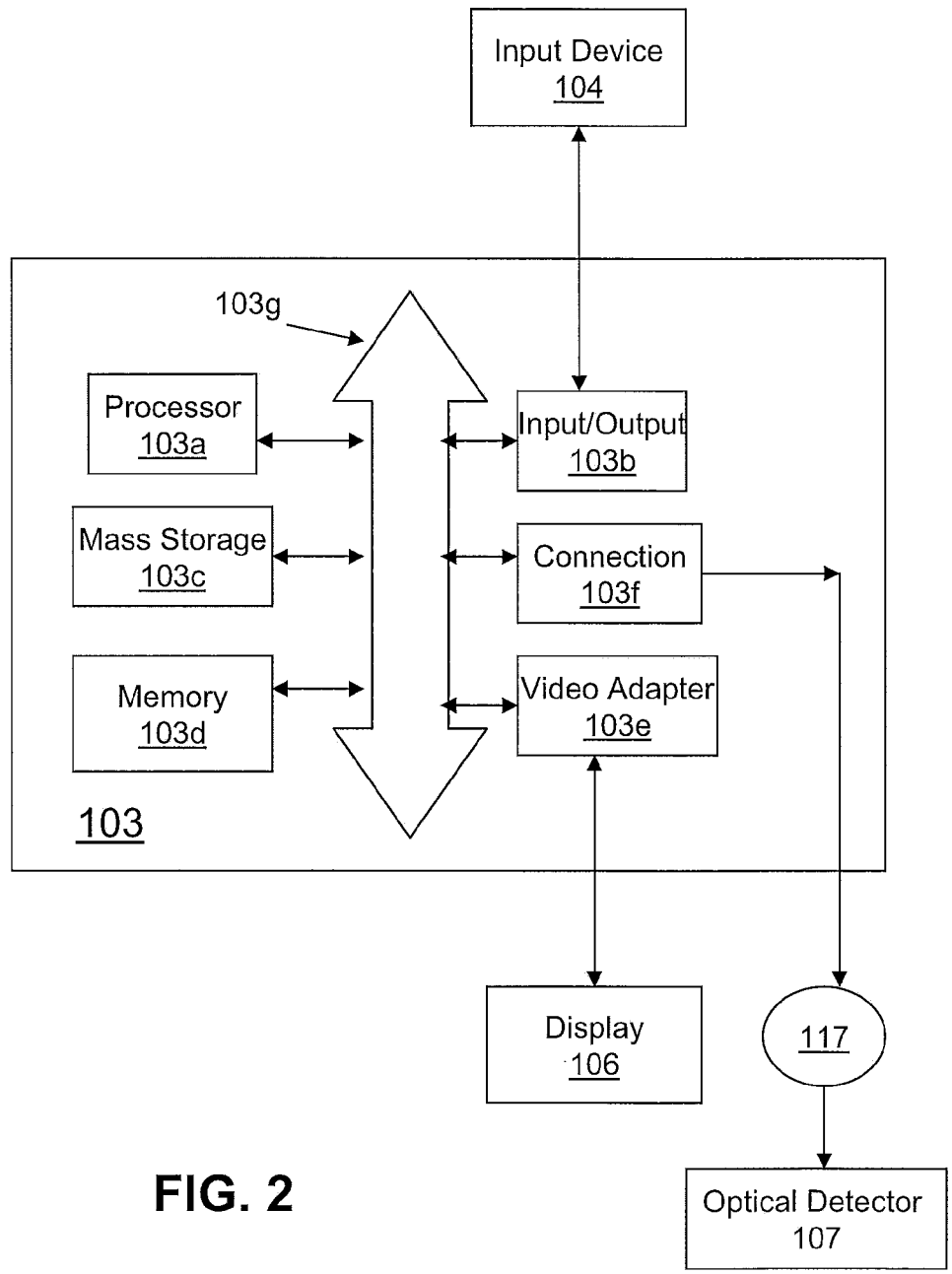
FIG. 2 is a schematic diagram of an image receiving device of the segmentation system of FIG. 1 in accordance with the invention.

FIG. 2 illustrates a schematic diagram of the image receiving device of the segmentation system of FIG. 1. Imaging receiving device 103 includes the typical components associated with a conventional computer. The imaging receiving device 103 includes: a processor 103a, an input/output (I/O) controller 103b, a mass storage 103c, a memory 103d, a video adapter 103e, a connection interface 103f and a system bus 103g that operatively, electrically or wirelessly, couples the aforementioned systems components to the processor 103a. Also, the system bus 103g, electrically or wirelessly, operatively couples typical computer system components to the processor 103a. The processor 103a may be referred to as a processing unit, a central processing unit (CPU), a plurality of processing units or a parallel processing unit. System bus 103g may be a typical bus associated with a conventional computer. Memory 103d includes a read only memory (ROM) and a random access memory (RAM). ROM includes a typical input/output system including basic routines, which assists in transferring information between components of the computer during start-up.

Above the memory 103d is the mass storage 103c, which includes: 1. a hard disk drive component (not shown) for reading from and writing to a hard disk and a hard disk drive interface (not shown), 2. a magnetic disk drive (not shown) and a hard disk drive interface (not shown) and 3. an optical disk drive (not shown) for reading from or writing to a removable optical disk such as a CD-ROM or other optical media and an optical disk drive interface (not shown). The aforementioned drives and their associated computer readable media provide non-volatile storage of computer-readable instructions, data structures, program modules and other data for the computer 103. Also, the aforementioned drives include the preparation of an image for segmentation image algorithm, software or equation of this invention or a preprocessing operation for the image, which will be described in the flow chart of FIG. 4 that works with the processor 103 to reconstruct an image of living cells. In another embodiment, the preparation of an image for segmentation algorithm, software or equation may be stored in the processor 103a, memory 103d or any other part of the image receiving device 103 known to those of ordinary skill in the art.

Input/output controller 103b is connected to the processor 103a by the bus 103g, where the input/output controller 103b acts as a serial port interface that allows a user to enter commands and information into the computer through input device 104, such as a keyboard and pointing devices. The typical pointing devices utilized are joysticks, mouse, game pads or the like. A display 106, is electrically or wirelessly connected to the system bus 103g by the video adapter 103e. Display 106 may be the typical computer monitor, Liquid Crystal Display, High-Definition TV (HDTV), projection screen or a device capable of having characters and/or still images generated by a computer 103. Next to the video adapter 103e of the computer 103, is the connection interface 103f. The connection interface 103f may be referred to as a network interface which is connected, as described above, by the communication link 117 to the optical detector 107. Also, the image receiving device 103 may include a network adapter or a modem, which enables the image receiving device 103 to be coupled to other computers.

Figure 3:
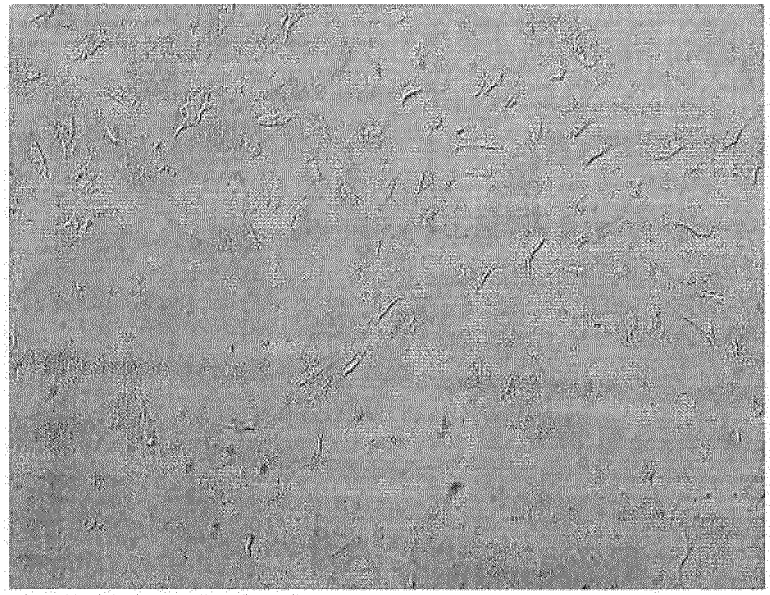
FIG. 3 is an example of a brightfield image in accordance with the invention.

FIG. 3 is an example of an image that is segmented and reconstructed. This image is an example of a typical brightfield image described above. This particular brightfield image depicts live cells, but brightfield images may depict biological organisms, nucleic acid, organic tissue or the like. The live cells to be inspected are normally placed on a clear glass slide and light is transmitted through the cells, which makes the cells appear against a bright background hence the term "brightfield." The cells in the light path are seen because natural pigmentation or stains absorb light differentially, or because they are thick enough to absorb a significant amount of light despite being colorless. The interior of the cells in the brightfield image is barely discernible so one can not tell the difference between the cells and the background. The digital images of the specimens that were captured by using the microscope system 101 at a variety of zoom optical system magnifications. The image was corrected and adjusted with respect to contrast, brightness, sharpness, hue, color balance, and saturation using digital image processing tools available on software stored in computer 103.

For this depiction of the live cells, an interior of the cells is barely discernible because of the difference in texture. There is an implicit assumption that the gray level intensity between the background and the cell is sufficiently different to admit segmentation by thresholding intensities only. Variations on this theme using edge detection filters or seeded region growing does not penetrate through to the core issue of blindness to texture. The transmitted light images of the cells could be best described as metallic gray blobs on a metallic gray background. Often these cells are only visible because of the whiteness/blackness of the cells' walls and a barely discernible difference in graininess between the inside of the cells and the background. Typically noise levels are severe.

FIG. 4 is a flow chart that depicts an example of how an image is prepared for segmentation. This operation of the preparation for segmentation of an image refers to preparing a brightfield image of FIG. 3 for segmentation, but this preparation for segmentation system also may be utilized to prepare the following types of image for segmentation: a transparent image, a phase contrast image, a differential-interference-contrast (DIC) microscopy image, any image associated with a microscope system 101 or a high throughput assay 101, any type of pixel generated image or any image. An image of the sample specimen 115 (FIG. 1) is taken by optical detector 107 of the image transmitting device 101. Also, this preparation for segmentation system refers to a software, algorithm or equation of this invention stored on mass storage 103c that works with the processor 103 labels regions of the living cells and prepares a simplified model of the image wherein neighboring pixels are labeled to the same. In another embodiment, the preparation for segmentation image algorithm, software or equation may be stored in the processor 103a, memory 103d or any other part of the image receiving device 103 known to those of ordinary skill in the art. In yet another embodiment, the preparation for segmentation software, algorithm or equation is stored on a computer-readable medium that includes computer-executable instructions. The computer-readable medium includes a floppy disk, optical disc, digital video disk, computer disk read only memory (CD-ROM) and the like.

At block 401, the image is transferred by the optical detector 107 through the communication link 117 by the connection interface 103f (FIG. 2) where the image is received at the image receiving device 103. Next, at block 403, a Dual Tree Wave Complex Transform (DTWCT) is applied to the image.

Figure 6:
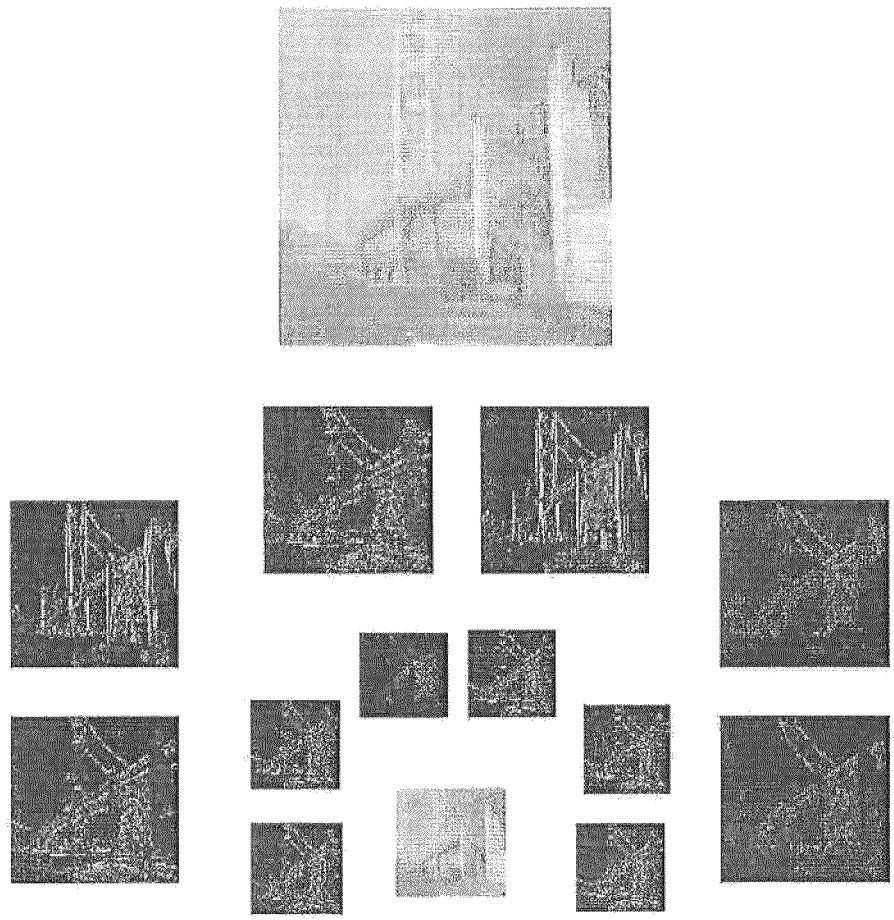
FIG. 6 illustrates an example image and decompositions of the image into sub-images in accordance with the invention.

The image is transformed by utilizing the Dual Tree Complex Wavelet Transform (DTWCT). At DTWCT, the image received at the image receiving device 103 is decomposed into two to twelve sub images or plurality of sub images by applying and providing the known Dual Tree Complex Wavelet Transform. Hatipoglu, Serkan, Kingsbury Nick and Mitra Sanjit, "*Texture Classification Using Dual-Tree Complex Wavelet Transform*", Image Processing and Its Applications, Conference Publication No. 465, 1999 which is herein incorporated by reference. Preferably, the image is decomposed into six sub-images based on a set of filters or a plurality of filters that are repeatedly applied to the image to discern details of the image at different scales. The number of filters repeatedly applied to the image can be from two to twelve filters. Preferably, six filters are repeatedly applied to filter the image into six sub images. For example, six sub-images of an image of a bridge, as shown in FIG. 6, are taken based on the image being applied to filters of low pass filters and high pass filters or any other combination thereof depending on the person utilizing the pointing device 104 (FIG. 2) to determine what filters should be utilized to filter the image. The filters can also be quadrature shifting filters, odd length biorthogonal filters, LeGall filters, Near-Symmetric filters, Antonini filters, quarter sample shift orthogonal filters, complex filters and the like.

The high pass filter discerns fine detail of the image and low pass filter sees the average behavior of the image. These filters are chosen so that the combination of low and high pass images will result in a reconstruction of the original image where no information is lost. Thereafter, for this process it is normal to repeat the process by utilizing only the low pass filter component. These 6 sub images for the low pass filter are repeatedly broken down into smaller and smaller components, which constitute the typical pyramid decomposition as shown in FIG. 6. This breakdown of sub images is the standard recursive breakdown of low pass sub-images. Alternatively, other types of recursive breakdown of low pass sub-images include quadtree decomposition that can also be utilized by this embodiment.

At this point, after the six sub images are filtered with a plurality of low pass and a plurality high pass filters in any combination thereof, then the six sub-images are filtered with complex conjugates of the column and rows filters. These six sub images are in two adjacent spectral quadrants, having real and imaginary coefficients, which are oriented at angles from left to right −15 degrees, −45 degrees, −75 degrees, 75 degrees, 45 degrees and 15 degrees as shown in FIG. 7. The strong orientation occurs because the complex filters are symmetry responses. These complex filters can separate positive frequencies from negative ones vertically and horizontally so positive and negative frequencies are not aliased.

At each level, application of the DTCWT yields six detail images (high pass images) and one smooth image (low pass image). The DTCWT is further applied to the smooth image to yield six more detail images at the next level and yet another, smaller, smooth image. The process can be repeated to some predetermined number of levels. Each level corresponds to a different scale. The first time the DTCWT is applied the six detail images comprise the finest detail only viewable at the highest magnification. Cell structures at this scale could comprise granules and mitochondria, for example. The next application of the DTCWT will yield features at a lower order of detail, such as nuclei, for example. If one were to rescale the image of the bridge at the bottom it would be very blurry since this is an image of the bridge where all the detail has been taken out. From our point of view, where we are interested in texture, it makes sense to combine the detail images at each level (or scale) to yield a single image. We have no interest in orientation of the texture but rather, wish to derive a measure of texture that is independent of position and orientation. The Dual Tree Complex Wavelet Transform offers several benefits. First, the transform provides approximate shift invariance. In addition, the transform provides good directional selectivity in 2D Gabor like filters. The selectivity provides some sensitivity to shape and edges of the living cells of sample specimen 115 that will be depicted in the reconstructed image of the sample specimen 115 so the true shape of the living cells may be shown, which depicts the texture of the sample specimen. Next, the image of the living cells is improved by using the short linear phase filters associated with the Dual Tree Complex Wavelet Transform. Linear phase avoids phase distortion by making phase changes introduced by the filter proportional to frequency. The term "short" refers to fast because less computation is involved when using short filters. Further, redundancy in a wavelet transform, whilst bad in image compression, can be good for avoiding artifacts. It is this property that leads to translation variance. Lastly, this transform has directionality that is good because it avoids checkerboard artifacts that occur when using horizontal/vertical filters.

Figure 8A:
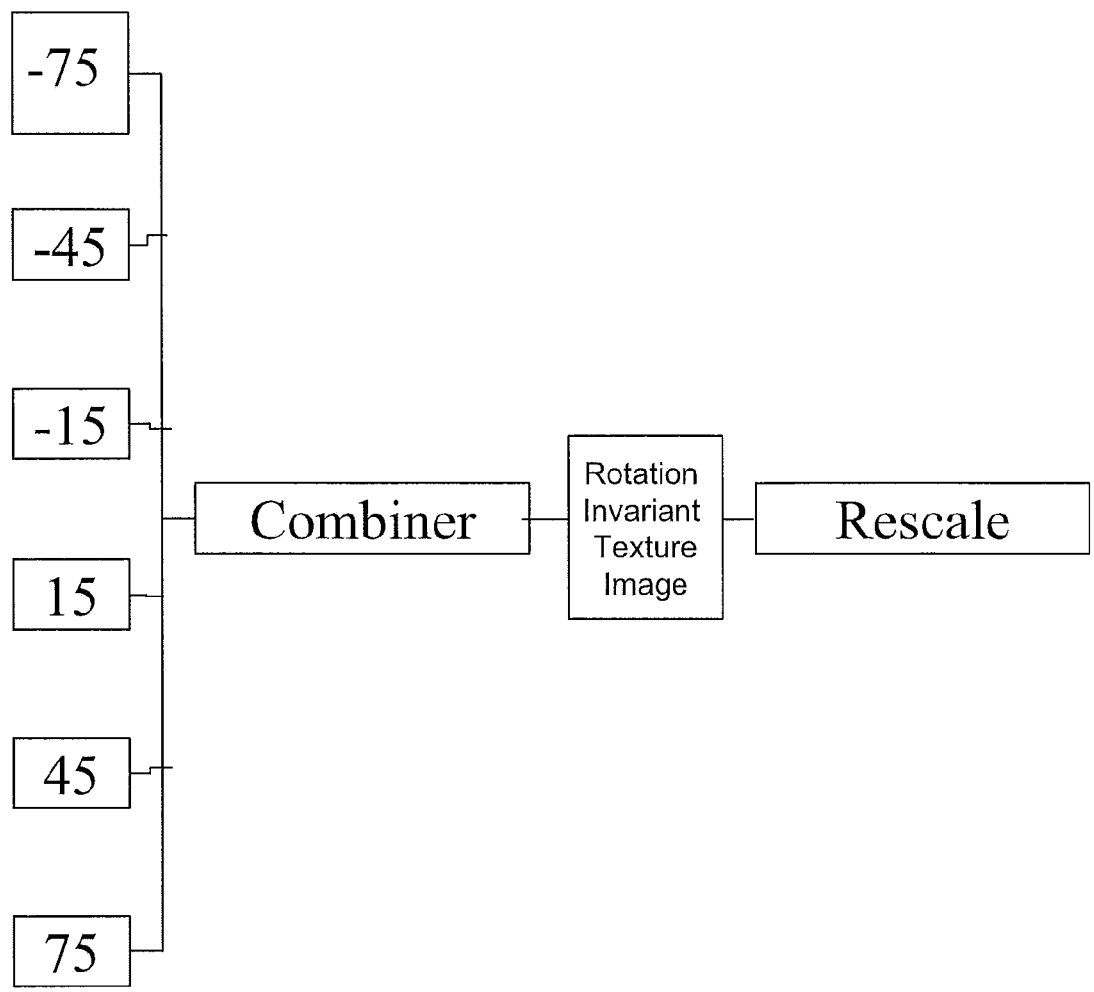
FIG. 8A depicts a resealing of the high pass filter six sub-images in accordance with the invention.
Figure 8B:
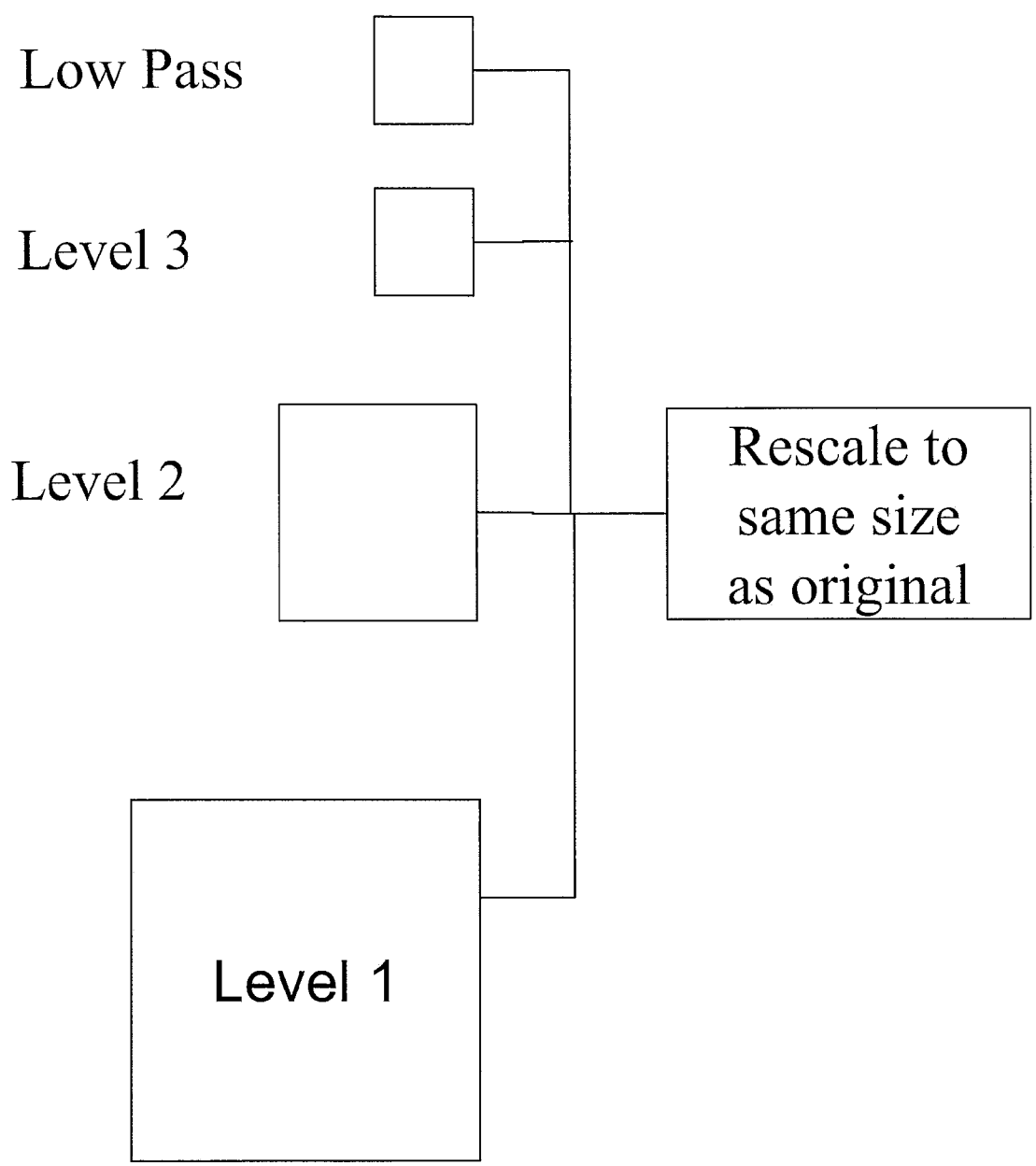
FIG. 8B depicts a resealing of the low pass filter sub-image in accordance with the invention.

At this point, we have 6 detail images corresponding each level with each of the six images corresponding to details at orientations of 75, 45, 15, −15, −45, −75 degrees as shown in FIG. 6. At block 405, the method used to generate invariant representation is as follows; At each level of the pyramid decomposition, the response of the 6 high pass sub-images is combined in some non-order specific manner to make a composite image of the same size as in FIG. 8A. The resultant image is approximately rotationally invariant. To combine the images one may choose the sum of the absolute values, this being independent of order. Another choice would be the maximum value of the 6. The sum of the squares is another option. The resultant image has to be resized to the size of the original image to facilitate the construction of feature vectors (as discussed later). There are several typical methods that may be utilized for image resizing, which range from the standard methods such as nearest neighbors, bilinear or bicubic resizing to the more exotic methods using image transformations such as the Discrete Cosine Transform (DCT) and Fast Fourier Transform (FFT). The inverse DTCWT can also be used to resize sub-images. In this case, all the sub-images are set to zero except the current image. The result of the inverse DTWCT image rescaled will show the individual contribution of the current sub-image to in comparison to the original image at full size where detail is preserved. The last choice of resizing algorithm would be the choice of the purist. Also, using the aforementioned resealing methods utilized for the 6 high pass images as shown in FIG. 8B also rescales the low pass image.

At block 407, the high pass image and the low pass image are combined to implement deshading as well as a certain degree of cell declumping. The symbol H refers to the high pass image and L refers to the low pass image. Also, FIG. 3 illustrates a DIC image that includes noise and the creases that will be removed by using deshading. In its simplest form, we would simply compute the dimensionless quantity H/L. This measure has a serious drawback of dividing by a quantity that may decrease to zero or to a number close to zero. A better solution is to compute $I_{BF}$ as shown below. $I_{BF}$ represents the output of a pseudo-fluorescent image, H represents the high pass filtered image, L represents the low pass filtered image and a is a parameter that depends on noise levels of the image L image as shown in the following equation:

$$I_{BF} = \frac{L}{L^2 + a^2} \cdot H$$

The astute reader will recognize the similarity to a Wiener Filter (The Wiener Filter is the optimal Least Squares solution used in inverse filtering that avoids dividing by zero). This is a dimensionless quantity that is independent of multiplicative variations in image intensity across the image. Moreover, when L is zero $I_{BF}$ is also zero. This last point actually helps to declump cells which otherwise would be joined because high pass filters would mistakenly see cell boundaries as texture. Thus, the low pass image and the high pass image are recombined to form a pseudo-fluorescent image at block 409.

Feature vectors are derived from the approximately rotation invariant features constructed above when sub-images were resized to the size of the original image. For each pixel in the original image there is a corresponding feature in each rotationally invariant sub-image. Therefore, we can define a feature vector for each pixel in the original image by selecting as an element the corresponding pixel in each of the rescaled images.

The pixel of a pseudo-fluorescent image is derived from the corresponding feature vector by a simple feature summarization process. The feature vectors yielded by the procedure described herein can be summarized in one dimensional form by the vector magnitude. This quantity suffices to distinguish cell constructs from image background. More generally, the feature extraction process entails extracting the raw data from the image or array of pixels and defining an attribute of the image or array of pixels such as a location where cells are located on the array of pixels. For example, the location of a certain array of pixels may be on a top portion or a bottom portion of the image. The top and bottom portion of the image containing the array of pixels will be assigned a class or labeled. At this point the magnitude of the feature vector is obtained. Each vector is classified so that each point in the vector is able to form a reconstructed image of the brightfield image of FIG. 3. There are several different well known methods employed to classify the vectors, such as clustering feature vectors, mapping plurality of feature vectors to 1-dimensional space and utilizing Markov Random Fields. For this embodiment, mapping feature vector to 1D will be utilized where each vector is translated into a single number. In another embodiment, a combination of the aforementioned well known methods used to employ to classify the vectors may be employed to transform the vector into a single number. In yet another embodiment of the invention, the feature vectors may be clustered using a priority queue where a seeded region growing algorithm can be implemented by placing image pixels (and their corresponding feature vectors) on the queue and growing them according to fitness. The fitness measure depends on the similarity of feature vectors in neighboring pixels to the feature vector of the current pixel. Feature vectors may also be clustered using standard techniques such as K-means, bisecting K-means or support vector machines. In yet another embodiment, the standard method of seeking a good solution as opposed to an optimal solution for clustering feature vectors occurs by sampling from the Posterior Distribution using Gibbs sampling or some other means of sampling a posterior density, which is familiar method known to those ordinary skill in the art.

Optionally, a typical BayesShrink denoising procedure is performed. The combination of the DTWCT with the BayesShrink denoising procedure of wavelet shrinkage is an effective way to denoise a wide variety of biological images including both brightfield and fluorescent. BayesShrink denoising is an adaptive data-driven threshold for image denoising via wavelet soft-thresholding. Also, BayesShrink denoising shrinks magnitude of wavelets, so the small noisy ones end up having a zero magnitude. We assume generalized Gaussian distribution (GGD) for the wavelet coefficients in each detail subband. We then try to find the threshold T that minimizes the Bayesian Risk. This BayesShrink denoising equation is utilized to remove noise from the image. Raghuram, Rangarajan, Ramji Venkataramanan, Siddarth Shat, *Image Denoising Using Wavelets: Wavelets & Time Frequency*" p 1-15, December 2002 which is herein incorporated by reference. For BayesShrink denoising, a threshold for each subband assuming a Generalized Gaussian Distribution (GGD) is determined. The GGD is given by:

$$GG_{\sigma x, \beta}(x) = C(\sigma x, \beta) \exp - [\infty(\sigma x, \beta)|x|]^\beta - -\infty < x < \infty, \beta > 0, \text{ where}$$

$$\infty(\sigma x, \beta) = \frac{-1}{\sigma x} \frac{[\Gamma(3/\beta)]^{1/2}}{[\Gamma(1/\beta)]} \text{ and } C(\sigma x, \beta) = \frac{\beta \infty(\sigma x, \beta)}{2\Gamma(1/\beta)}$$

$$\text{and } \Gamma \int^\infty e^{-u} u^{t-1} du.$$

The parameter σx is the standard deviation and β is the shape parameter. It has been observed that with a shape parameter β ranging from 0.5 to 1, which describes the distribution of coefficient in a subband for a large set of natural images. Assuming such a distribution for the wavelet coefficients, the empirically estimated β and σx for each subband and try to find the threshold T which minimizes the Bayesian Risk, i.e., the expected value of the means square error. $_T(T) = E(X-X)^2 = E_x E_{y|x}(X-X)^2$ where $X=\eta_T(Y)$, $Y|X \ N(x,o^2)$ and $X \ GG_{x,\beta}$. The optimal threshold T* is then given by $T*(_{\sigma x},\beta)$ =argmin$_T$(T). This is a function of the parameters σ$_x$, and β. Since there is no closed form solution for T*, numerical calculation is used to find its value. It is observed that the threshold value set by $$T_B(\sigma_x) = \frac{\sigma^2}{\sigma_X}$$

is very close to T*. The estimated threshold $T_B = \sigma^2/\sigma_x$ is not only nearly optimal but also has an intuitive appeal. The normalized threshold, $T_B/\sigma^2$ is inversely proportional to σ, the standard deviation X, and proportional to σ$_x$, the noise standard deviation. When σ/σ$_x$<<1, the signal is much stronger than the noise, $T_b/\sigma$ is chosen to be small in order to preserve most of the signal and remove some of the noise; when σ/σ$_x$>>1, the noise dominates and the normalized threshold is chosen to be large to remove the noise which has overwhelmed the signal. Thus, this threshold choice adapts to both the signal and the noise characteristics are reflected in the parameters σ and σ$_x$. The GGD parameters, σ$_x$ and β need to be estimated to compute $T_B(\sigma_x)$. The noise variance σ² variance σ² is estimated from the subband HH$_1$ by the robust median estimator $$v = \text{vector}\begin{pmatrix}\text{for all values of all coefficients}\\ \text{at some current sublevel}\end{pmatrix}$$

$$\sigma_R = \frac{\text{median }(v)}{.6745}$$

$$m_2 = \frac{1\sum vi^2}{N} \text{(second moment)}$$

$$\sigma_X = \max(0, \sigma_y^2 - \sigma_R^2)$$

$$\sigma_R^2/\sigma_X \text{ or } \infty\text{(no threshold)}$$

The feature vectors are compressed into a plurality of pixels whose brightness depends on local texture. For this embodiment, mapping feature vector to 1 dimension will be utilized where each vector is translated into a single number. This particular translation of a vector into a single number is utilized in conjunction with the well known Mahalanobis Distance. Each feature vector of the plurality of low frequency sub-images and plurality of high frequency sub-images are illustrated by the values v1 and v2 (v) representing typical x and y coordinates on a 2-dimensional graph as shown in FIG. 5A where the feature vectors form an ellipsoidal shape. Even though an ellipsoidal shape is utilized in this example the feature vectors of the image may form any shape. In order to change this value feature vector v into an image the standard Mahalanobis equation is utilized to produce associated whitened feature vectors w1 and w2 (w), representing typical x and y components on a 2-dimensional graph where w correlates to the value v as shown in FIG. 5B. The Mahalanobis metric is used as a means to convert feature vectors into a representation where one can calculate the magnitude of a feature vector. The feature vectors v are changed into whitened feature vectors w where the image depicted has a circular shape. Circles are associated with an L2 norm (or Euclidean norm) one could substitute other shapes such as square (L infinity or Metropolis norm) or diamond (L1 norm) in place of the circular shape in order to depict the change of the featured vectors v to the whitened feature vectors w. This Mahalanobis distance equation computes covariance matrix (C$^{-1}$) of features of the vector whitens feature vectors and normalizes the feature vectors. The covariance matrix is a matrix of covariances between elements of the feature vector v. Covariance is the measure of how much two variables vary together, which means the covariance becomes more positive for each pair of values which differ from their mean in the same direction, and becomes more negative with each pair of values which differ from their mean in opposite direction. In this way, the more often they differ in the same direction, the more positive the covariance, and the more often they differ in opposite directions, the more negative the covariance. After applying a whitening transform the covariance matrix is, by definition, given by the identity matrix.

The following formula is utilized to convert the feature vector v into whitened feature vector w, P$^T$ is the matrix of eigenvectors and Λ is a diagonal matrix of eigenvalue.

C=PΛ P$^T$ w=Λ$^{-1/2}$ P$^T$v when there is x correlation (FIG. 5A)

w=Λ$^{-1/2}$ v when there is no x correlation

It would be well known to one skilled in the art that other whitening procedures exist, based on matrix square roots, such as the Cholesky decomposition.

Figure 11A:
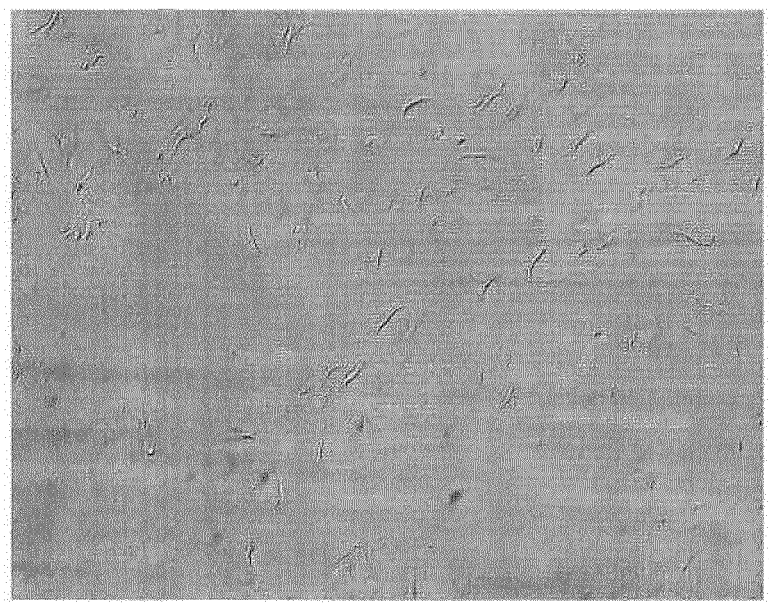
FIG. 11A illustrates an image of FIG. 3, where the noise has been removed.
Figure 11B:
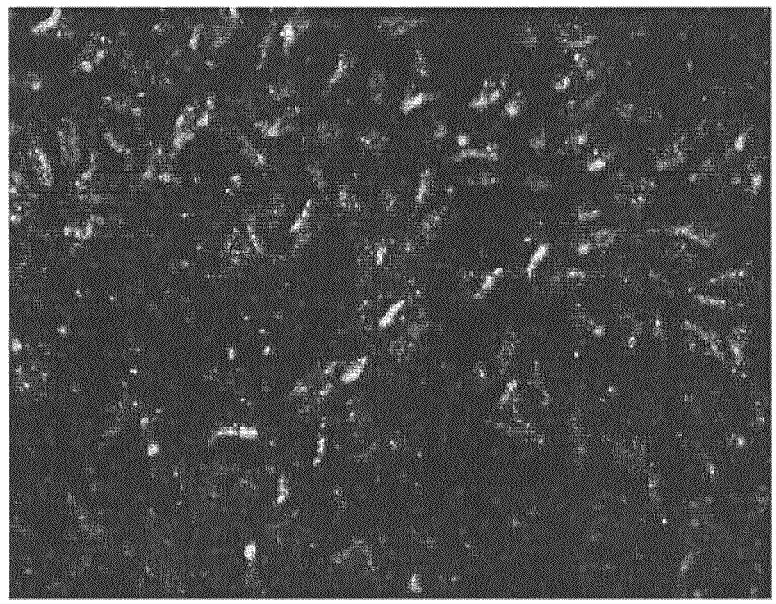
FIG. 11B illustrates a pseudo-fluorescent image of FIG. 11A, where this pseudo-fluorescent image is in a form suitable for segmentation using techniques developed for processing fluorescent (stained) images.

The image displayed on the computer 103 is a pseudo-fluorescent image, as shown in FIGS. 10A and 10B. FIG. 10A illustrates a pseudo-fluorescent image in a software program, for example Developer Toolbox counting of nuclei that went through the process associated with FIG. 4, where the white spaces indicates the actual cells and cells counted. The whiteness is due to the energy in the texture. This texture is detected by the DTCWT. This image is ready for segmentation using the same techniques as used for segmenting fluorescent images that already exist in microscopy software (such as MCID or Developer from Amersham-GE Healthcare.). Similar to FIG. 10A, FIG. 10B illustrates another pseudo-fluorescent image in a software program, for example Developer Software Tool box that went through the process associated with FIG. 4, where the lines indicate the actual cell shapes. This pseudo-fluorescent image of the living cells can then be segment by the typical segmentation process. When these cells are segmented a person can obtain, a cell count, cell size, cell shape, shape distribution, cell functions and the typical results associated with being able to discern living cells from the background. FIG. 11B illustrates a DIC pseudo-fluorescent image where cells appears as white on a black background. The whiteness is due to energy in the texture. The texture is detected by the DTCWT. This image is ready for segmentation using the same fluorescent images that already exist in the software. Next, optionally at block 411 the pseudo-fluorescent image is denoised.

Figure 9A:
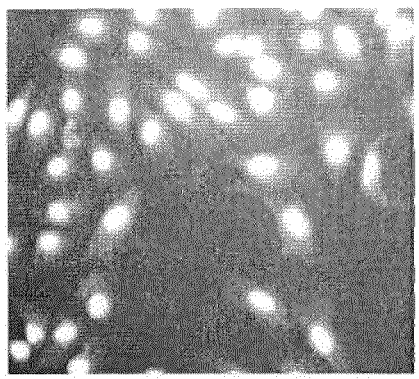
FIG. 9A illustrates a cytoplasm image with noise in accordance with the invention.
Figure 9B:
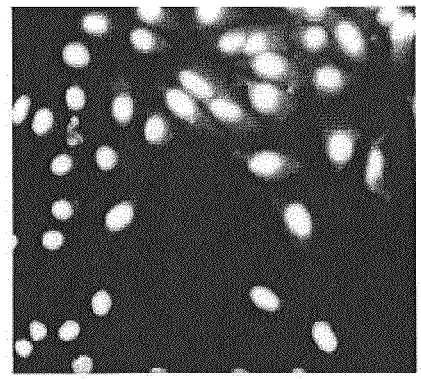
FIG. 9B illustrates the cytoplasm image of FIG. 9A where noise has been removed in accordance with the invention.

Next, the pseudo-fluorescent image is optionally denoised at block 411. The pseudo-fluorescent image is denoised by utilizing a denoising algorithm that includes the DTCWT (discussed above), Bayes Shrink procedure (discussed above) and an inverse DTCWT. FIG. 9A illustrate cytoplasm that includes noise and FIG. 9B illustrates the same cytoplasm where noise has been removed by the aforementioned process. This view of the cytoplasm enables one to count the cells that are in the specimen and discern the cells from the background of the specimen. FIG. 11A illustrates a denoised image of the DIC image of FIG. 3 showing how glossy and smooth it is. After the pseudo-fluorescent image is denoised then at block 413 the pseudo-fluorescent image is able to be segmented by utilizing a typical segmentation method.

This invention provides a system that allows a user to simply prepare an image, such as brightfield image for segmentation. A user is able to prepare an image for segmentation by applying a Dual Tree Complex Wavelet transform and a BayesShrink denoising procedure, then assigning labels to vectors of the image to form a pseudo-fluorescent image. Also, the user is able to utilize a denoising algorithm to remove noise from the pseudo-fluorescent image before the pseudo-fluorescent image is segmented by a typical segmentation process.

It is intended that the foregoing detailed description of the invention be regarded as illustrative rather than limiting and that it be understood that it is the following claims, including all equivalents, which are intended to define the scope of the invention.

What is claimed is:

1. A system for preparing a non-fluorescent image of a cell for segmentation, comprising:
   an image transmitting device configured to transmit a first image to an image receiving device;
   the image receiving device configured to:
   receive the first image;
   apply, at a first level, a Dual Tree Complex Wavelet transform to the first image to form a plurality of high pass sub-images each corresponding to details at a different orientation and one low pass image;
   apply, at a predetermined number of subsequent levels, the Dual Tree Complex Wavelet transform to the low pass image of the preceding level to form a plurality of high pass sub-images each corresponding to details at a different orientation and one low pass image, wherein each level corresponds to a different scale;
   combine and rescale the low pass images of each level to form a rescaled and combined low pass image;
   generate a rotational invariant resultant image based on combining the plurality of high pass sub-images of each level;
   rescale the rotational invariant resultant image to the same size as the first image;
   generate a feature vector for each pixel in the first image based on the rescaled rotational invariant resultant image;
   form a pseudo-fluorescent image based on re-combining the rescaled rotational invariant resultant image with said rescaled and combined low pass image; and
   reconstruct pixels of the pseudo-fluorescent image from the corresponding feature vector.

2. The system of claim 1, wherein the image receiving device is further configured to:
   provide a BayesShrink denoising procedure to the Dual Tree Complex Wavelet transform.

3. The system of claim 1, wherein the image receiving device is a high through-put screening device.

4. The system of claim 1, wherein the first image is a brightfield image.

5. The system of claim 1, wherein the image transmitting device is a fluorescent microscope.

6. The system of claim 1, wherein the feature vector is classified.

7. The system of claim 6, wherein Markov Random Fields are utilized to classify the feature vector.

8. The system of claim 1, wherein a plurality of feature vectors are compressed into a single image by utilizing a Mahalanobis Distance, wherein each of the plurality of feature vectors corresponds to a pixel in the first image based on the rescaled rotational invariant resultant image.

9. The system of claim 1, wherein the Dual Tree Complex Wavelet transform further comprises a plurality of filters configured to be applied to the first image to produce the plurality of high pass sub-images.

10. The system of claim 9, wherein the plurality of filters are from a group comprising low pass filters, high pass filters, quadrature shifting filters, LeGall filters, Near Symmetric filters, Antonini filters, quarter sample shift orthogonal filters, odd length biorthogonal filters and complex filters.

11. The system of claim 1, wherein the image transmitting device includes an optical detector.

12. The system of claim 11, wherein the optical detector is coupled to a communication link configured to transmit the first image to the image receiving device.

13. The system of claim 11, wherein the optical detector is a charge coupled device.

14. The system of claim 11, wherein the optical detector is a complementary metal-oxide semiconductor (CMOS) image detector.

15. The system of claim 1, wherein the image receiving device is further configured to segment the reconstructed pseudo-fluorescent image.

16. The system of claim 15, wherein the segmented pseudo-fluorescent image is utilized to obtain a cell count for cells shown in the segmented pseudo-fluorescent image.

17. The system of claim 16, wherein the segmented pseudo-fluorescent image is utilized to obtain a cell size for the cells shown in the segmented pseudo-fluorescent image.

18. An apparatus for preparing a non-fluorescent image of a cell for segmentation, comprising:
    a connection interface configured to receive a first image, the connection interface coupled to a mass storage, wherein the mass storage is configured to:
    receive the first image;
    apply, at a first level, a Dual Tree Complex Wavelet transform to the first image to form a plurality of high pass sub-images each corresponding to details at a different orientation and one low pass image;
    apply, at a predetermined number of subsequent levels, the Dual Tree Complex Wavelet transform to the low pass image of the preceding level to form a plurality of high pass sub-images, each corresponding to details at a different orientation and one low pass image, wherein each level corresponds to a different scale;
    combine and rescale the low pass images of each level to form a rescaled and combined low pass image;
    generate a rotational invariant resultant image based on combining the high pass images of each level;
    rescale the rotational invariant resultant image to the same size as the first image;
    generate a feature vector for each pixel in the first image based on the rescaled rotational invariant resultant image;
    form a pseudo-fluorescent image based on re-combining the rescaled rotational invariant resultant image with said rescaled and combined low pass image; and
    reconstruct pixels of the pseudo-fluorescent image from the corresponding feature vector.

19. The apparatus of claim 18, wherein the first image is a brightfield image.

20. The apparatus of claim 18, wherein the first image is a phase contrast image.

21. A method for preparing a non-fluorescent image of a cell for segmentation, comprising:
    receiving the first image;
    applying, at a first level, a Dual Tree Complex Wavelet transform to the first image to form a plurality of high pass sub-images each corresponding to details at a different orientation and one low pass image;
    applying, at a predetermined number of subsequent levels, the Dual Tree Complex Wavelet transform to the low pass image of the preceding level to form a plurality of high pass sub-images each corresponding to details at a different orientation and one low pass image, wherein each level corresponds to a different scale;

combining and resealing the low pass images of each level to form a resealed and combined low pass image;

generating a rotational invariant resultant image based on combining the high pass images of each level;

rescale the rotational invariant resultant image to the same size as the first image;

generating a feature vector for each pixel in the first image based on the resealed rotational invariant resultant image;

forming a pseudo-fluorescent image based on re-combining the resealed rotational invariant resultant image with said resealed and combined low pass image; and reconstructing pixels of the pseudo-fluorescent image from the corresponding feature vector.

22. The method of claim 21, wherein the dual tree complex wavelet transform utilizes a plurality of filters to decompose the first image into the plurality of high pass sub-images.

23. A non-transitory computer-readable medium comprising computer-executable instructions for preparing a non-fluorescent image of a cell for segmentation, the computer-executable instructions comprising:

receiving a first image;

applying, at a first level, a Dual Tree Complex Wavelet transform to the first image to form a plurality of high pass sub-images each corresponding to details at a different orientation and one low pass image;

applying, at a predetermined number of subsequent levels, the Dual Tree Complex Wavelet transform to the low pass image of the preceding level to form a plurality of high pass sub-images each corresponding to details at a different orientation and one low pass image, wherein each level corresponds to a different scale;

combining and resealing the low pass images of each level to form a resealed and combined low pass image;

generating a rotational invariant resultant image based on combining the high pass images of each level;

rescale the rotational invariant resultant image to the same size as the first image;

generating a feature vector for each pixel in the first image based on the resealed rotational invariant resultant image;

forming a pseudo-fluorescent image based on re-combining the resealed rotationally invariant resultant image with said resealed and combined low pass image; and reconstructing pixels of the pseudo-fluorescent image from the corresponding feature vector.

\* \* \* \* \*